United States Patent [19]

Doi et al.

[11] Patent Number: 5,289,374
[45] Date of Patent: Feb. 22, 1994

[54] METHOD AND SYSTEM FOR ANALYSIS OF FALSE POSITIVES PRODUCED BY AN AUTOMATED SCHEME FOR THE DETECTION OF LUNG NODULES IN DIGITAL CHEST RADIOGRAPHS

[75] Inventors: Kunio Doi; Tsuneo Matsumoto, both of Willowbrook; Maryellen L. Giger, Elmhurst; Akiko Kano, Willowbrook, all of Ill.

[73] Assignee: Arch Development Corporation, Chicago, Ill.

[21] Appl. No.: 843,715

[22] Filed: Feb. 28, 1992

[51] Int. Cl.⁵ .............. G06F 15/42; G06F 15/70; G06K 9/46
[52] U.S. Cl. .................. 364/413.13; 382/6; 364/413.01; 364/413.22; 364/413.23
[58] Field of Search ............ 364/413.13, 413.22, 364/413.23, 413.01; 382/6

[56] References Cited

U.S. PATENT DOCUMENTS

| | | | |
|---|---|---|---|
| 4,839,807 | 6/1989 | Doi et al. | 364/413.13 |
| 4,841,555 | 6/1989 | Doi et al. | 378/99 |
| 4,851,984 | 7/1989 | Doi et al. | 364/413.23 |
| 4,875,165 | 10/1989 | Fencil et al. | 364/413.22 |
| 4,907,156 | 3/1990 | Doi et al. | 364/413.13 |
| 4,918,534 | 4/1990 | Lam et al. | 358/225 |
| 5,003,979 | 4/1991 | Merickel et al. | 128/653 |
| 5,072,384 | 12/1991 | Doi et al. | 364/413.13 |
| 5,133,020 | 7/1992 | Giger et al. | 382/6 |
| 5,159,550 | 10/1992 | Sakamoto et al. | 364/413.13 |

OTHER PUBLICATIONS

"Mammogram Inspection by Computer"–Wolfgang Speisberger (IEEE Trans, on Biomed. Engr.–Apr. 1979); pp. 213–219.

Primary Examiner—Roy N. Envall, Jr.
Assistant Examiner—Joseph Thomas
Attorney, Agent, or Firm—Oblon, Spivak, McClelland, Maier & Neustadt

[57] ABSTRACT

A computerized method and system for reducing the number of false-positive detections of nodule candidates in the detection of abnormalities in digital chest radiography. The image is initially subjected to an image difference technique where the detection sensitivity is increased so as to avoid missing small nodules which might otherwise go undetected. Such a technique tends to increase the number of false-positives, however, leading to possible incorrect diagnoses of the radiographs. To reduce the number of false-positives, feature extraction techniques are applied to grown regions around the nodule candidates, in order to provide computer generated information concerning the candidates. A data base of parameters common to false-positives is compared to calculated parameters of a candidate of interest. The candidates with grown region parameters within the data base range common to false-positives are eliminated as being probable false-positive detections due to normal background anatomical features.

12 Claims, 21 Drawing Sheets

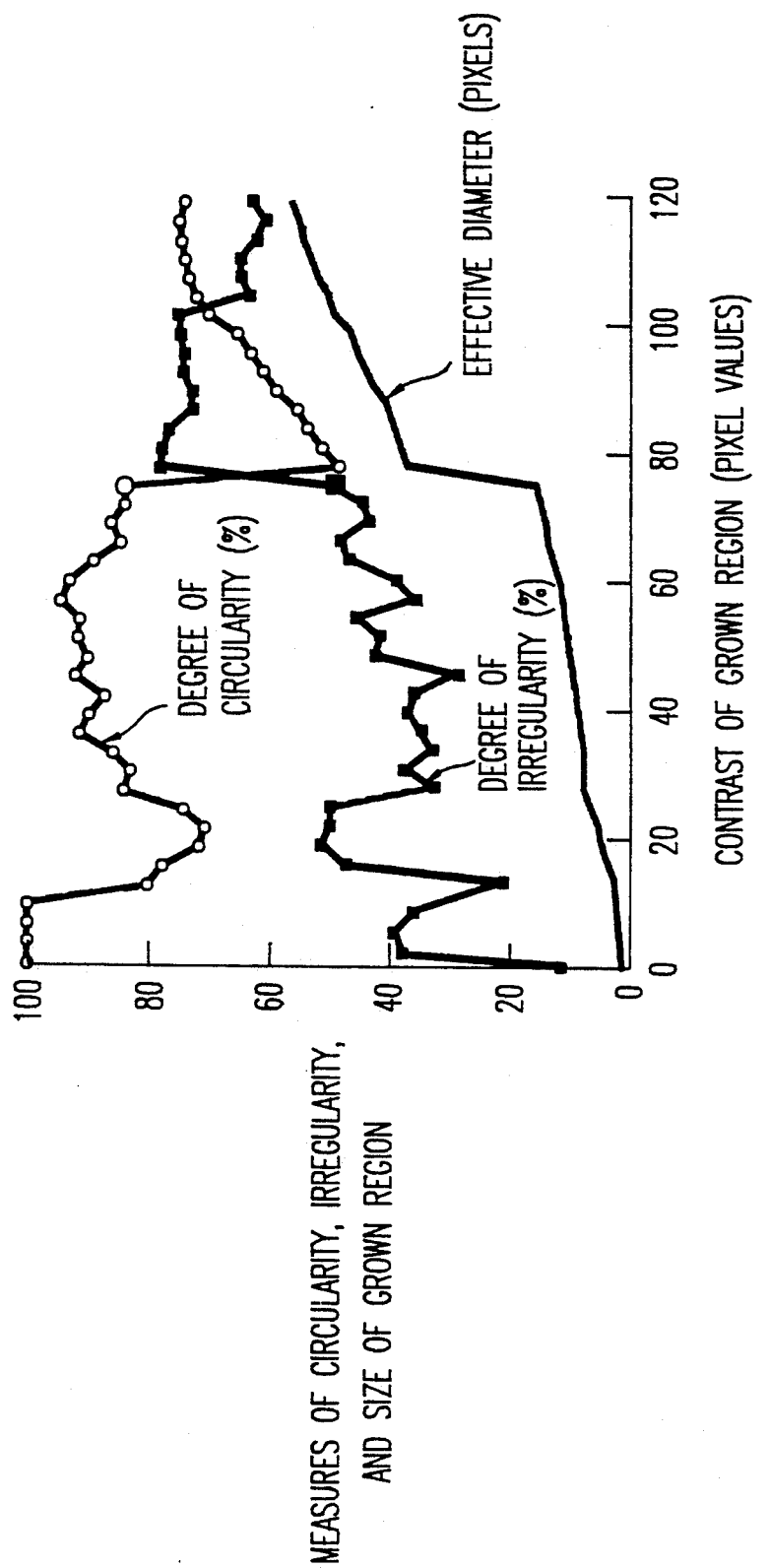

$$\text{EFFECTIVE DIAMETER} = 2\sqrt{\frac{\text{AREA OF GROWN REGION}}{\pi}}$$

$$\text{DEGREE OF CIRCULARITY} = \frac{\text{AREA OF GROWN REGION WITHIN CIRCLE}}{\text{AREA OF GROWN REGION}}$$

$$\text{DEGREE OF IRREGURALITY} = 1 - \frac{\text{PERIMETER OF CIRCLE}}{\text{PERIMETER OF GROWN REGION}}$$

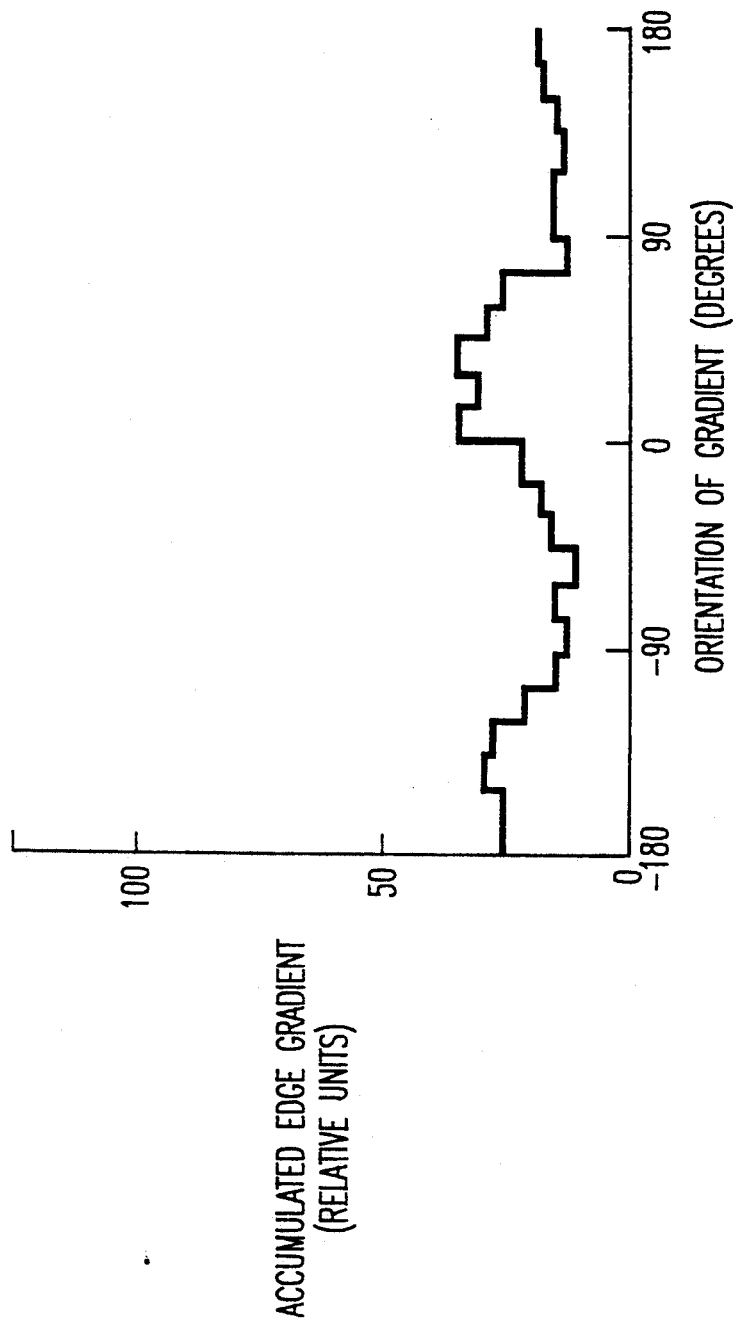

METHOD AND SYSTEM FOR ANALYSIS OF FALSE POSITIVES PRODUCED BY AN AUTOMATED SCHEME FOR THE DETECTION OF LUNG NODULES IN DIGITAL CHEST RADIOGRAPHS

The present invention was made in part with U.S. government support under grant number 2 R01 CA24806 from the Department of Health and Human Services and the National Cancer Institute, along with related copending application U.S. Ser. No. 07/843,721. The U.S. Government has certain rights in the invention.

BACKGROUND OF THE INVENTION

1. Field of the Invention

The invention relates to a method and system for reducing the number of false-positive detections of abnormalities in X-ray images by using digital image analysis techniques with a computerized scheme to analyze pulmonary nodule candidates or mammographic masses and microcalcifications for possible abnormality conditions indicative of disease.

2. Discussion of the Background

It is known that radiologists can fail to diagnose pulmonary nodules from chest radiographs in as many as 30% of positive cases. In addition, in a study by Muhm et al., Radiology, Vol. 148, pp. 609-615 (1983), it was reported that 90% of peripheral lung cancers were visible in retrospect on previous films. In order to alert the radiologist to locations of possible nodules or breast masses and microcalcifications, and to reduce the number of false-negatives diagnoses, the present inventors have developed a computer-aided diagnosis scheme for the detection of lung nodules in digital chest images and mammographic masses and microcalcifications. Such a computerized diagnosis scheme is disclosed in U.S. Pat. No. 4,907,156 to Doi et al, incorporated herein by reference.

The method and system are based on a difference-image approach in which a nodule-suppressed image is subtracted from a nodule-enhanced image in order to remove the complex background in a chest image, and thus enhance the conspicuity of nodules. After a difference image is obtained, feature-extraction techniques are employed which involve the size, contrast and shape of the nodule candidates. Using 60 clinical chest images, the sensitivity obtained with this previous method was approximately 70% at a false-positive rate of seven or eight per image. It is apparent that a practical limitation of this previous method is the existence of these false-positive detections which can lead to incorrect diagnoses by radiologists interpreting the computer generated data, i.e., a diagnosis of abnormality for an actually disease-free lung or breast.

In the prior art, a number of false-positives obtained with this computer scheme usually occurred at rib crossings, and at rib-and-vessel crossings. In addition, some end-on vessels and also aggregates of vessels produced false-positives. These normal anatomical background features will often appear similar to actual nodules (dense clusters of diseased cells) due to the shadows they produce on digitized chest X-rays using various gray levels. The different gray levels represent the level of opacity of the individual anatomical features. The image enhancement technique referred to above increases the sensitivity of the detection process, thus generating a higher number of possible actual nodule candidates. Such a technique is important so as not to miss any actual nodules which may be of relatively small size. In other words, the increased sensitivity reduces the number of false-negatives. However, the increased sensitivity tends to increase the number of false-positive detections as well by erroneously detecting normal background structures, commonly referred to as artifacts. Thus, one of the main concerns of the present invention is to be able to reduce the number of false-positive detections, while still maintaining the increased sensitivity.

SUMMARY OF THE INVENTION

Accordingly, one object of the present invention is to provide a novel method and system for improved techniques for discrimination between actual nodules and false-positives in a computerized detection scheme involved in digital chest radiology.

Another object of the present invention is to increase the nodule candidate detection sensitivity and then eliminate a variable number of the candidates based on predetermined information extracted by radiologists from experimental data.

A further related object is to perform feature extraction techniques on the nodule candidates to obtain information about the individual candidates and then to use this predetermined information to decide whether or not to remove the candidates as being false-positive detections.

Yet another object of the present invention is to eliminate additional false-positive candidates by applying a background trend correction technique to the digitized chest images after using a difference image technique, and then performing an edge gradient analysis on selected region of interest (ROIs) containing nodule candidates so as to generate further information indicative of false-positives.

These and other objects are accomplished by using a new, automated method and system for eliminating a number of false-positive nodule candidates using a region growing technique on identified candidates and then performing feature extraction techniques on the grown regions in order to determine information about the nodule candidates. This information includes such parameters as (1) the effective diameter of the grown regions, (2) the degree of circularity and (3) the degree of irregularity. Additional parameters such as the nodule candidate contrast, background contrast, edge gradient orientation and standard deviation of the gradient-orientation histogram are also determined to provide additional computer generated data information about the nodule candidates.

The candidates are initially selected after a chest radiograph is digitized and quantized, and then subjected to a difference image technique. Next, based on analysis of known false-positives by human observers, i.e., experienced radiologists, a number of the false-positives can be eliminated by comparison of their above mentioned parameters with predetermined parameters associated with known false-positives. These false-positives have parameter values outside a known range common to actual nodules (true-positives). Graphical analysis techniques were employed for human observer analysis in order to ascertain differences in parameter values for false-positives and actual nodules.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4c is a diagram indicating relationships between contrast of grown region and degree of circularity (circle), degree of irregularity (square), and effective diameter (solid line). The large circle, square, and X indicate the transition point;

FIG. 10b shows the gradient-orientation distribution of trend-corrected image of FIG. 10a;

FIG. 11b shows the gradient-orientation distribution of the trend-corrected region of FIG. 11a;

FIG. 12b shows the contour-line image without trend-correction for the image of FIG. 12a;

FIG. 13b shows the contour-line image without trend-correction for the image of FIG. 13a;

DETAILED DESCRIPTION OF THE PREFERRED EMBODIMENTS

Figure 1:
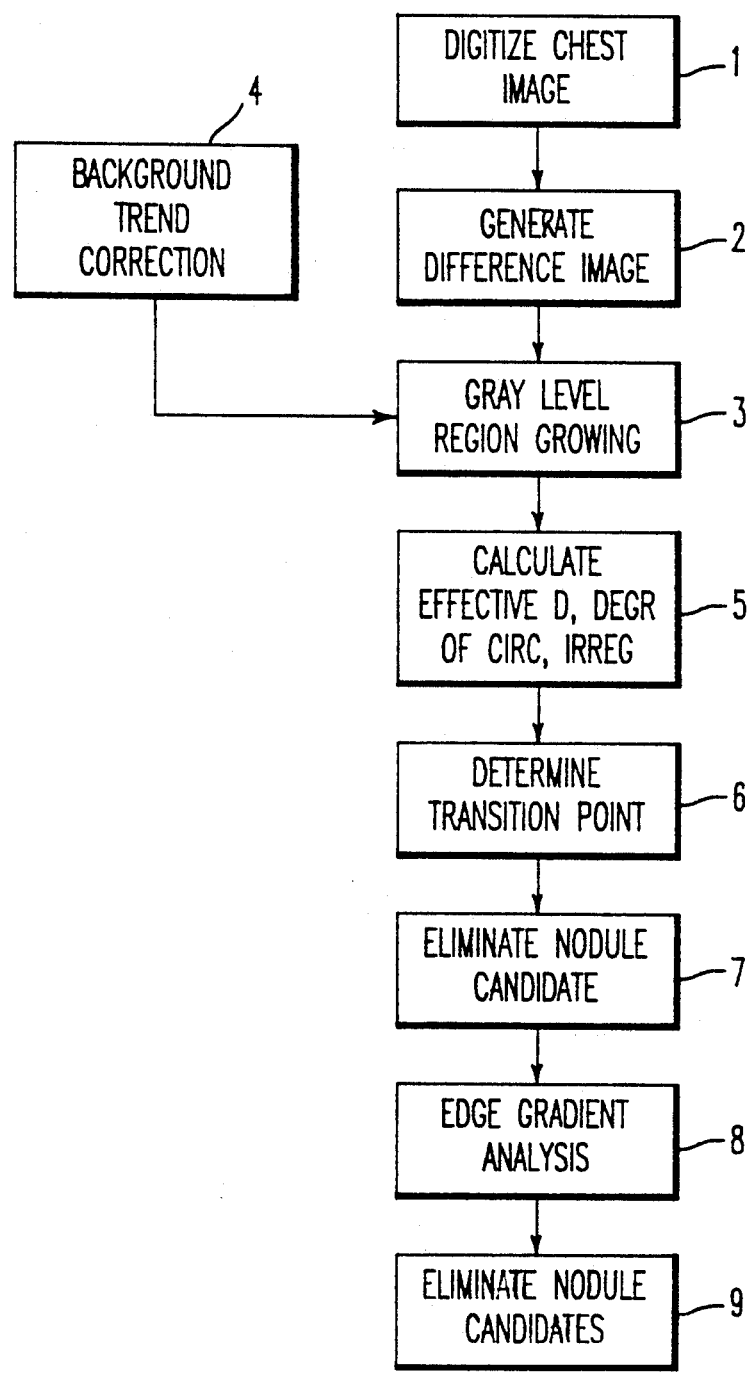
FIG. 1 is a flowchart illustrating the overall method used for the detection and elimination of false-positives in accordance with the present invention.

Referring now to the drawings, wherein like numerals designate identical or corresponding parts throughout the several views, and more particularly to FIG. 1 thereof, there is shown a block diagram representative of the overall scheme of the method of the present invention. Initially, a chest X-ray radiograph is digitized (block 1) using an optical drum scanner and thereafter the image is subjected to an image difference technique (block 2) for effecting nodule enhancement. Next, various gray-level regions are grown (block 3) which will be described in more detail later. A background trend correction technique is applied to the nodule candidate at this point for a first set of parameter calculations (block 4), using a two-dimensional surface fitting technique on the digitized chest image. For a second set of parameter calculations, no background trend correction is used, for reasons to be discussed later. For each of the grown regions, the parameters which are calculated include the effective diameter of the grown region, the degree of circularity and the degree of irregularity (block 5). From these computations, a transition point is determined (block 6). This point is defined as the point where the outermost grown region of a nodule candidate merges with the surrounding background contrast, as will be discussed below. The transition point data, i.e., the effective diameter, the degree of circularity and the degree of irregularity of the grown region at the transition point are used by a central processing means to determine if the nodule candidate should be eliminated based on predetermined parameter values of known false-positives, (block 7). An edge gradient analysis technique is then performed (block 8) by selecting 50×50 pixel regions of interest (ROIs) around the individual nodule candidates in order to determine additional edge gradient information about the candidate of interest. Those candidates exhibiting standard deviation values of edge gradient orientation above predetermined threshold values are then eliminated as being additional false-positive detections (block 9).

Figure 2:
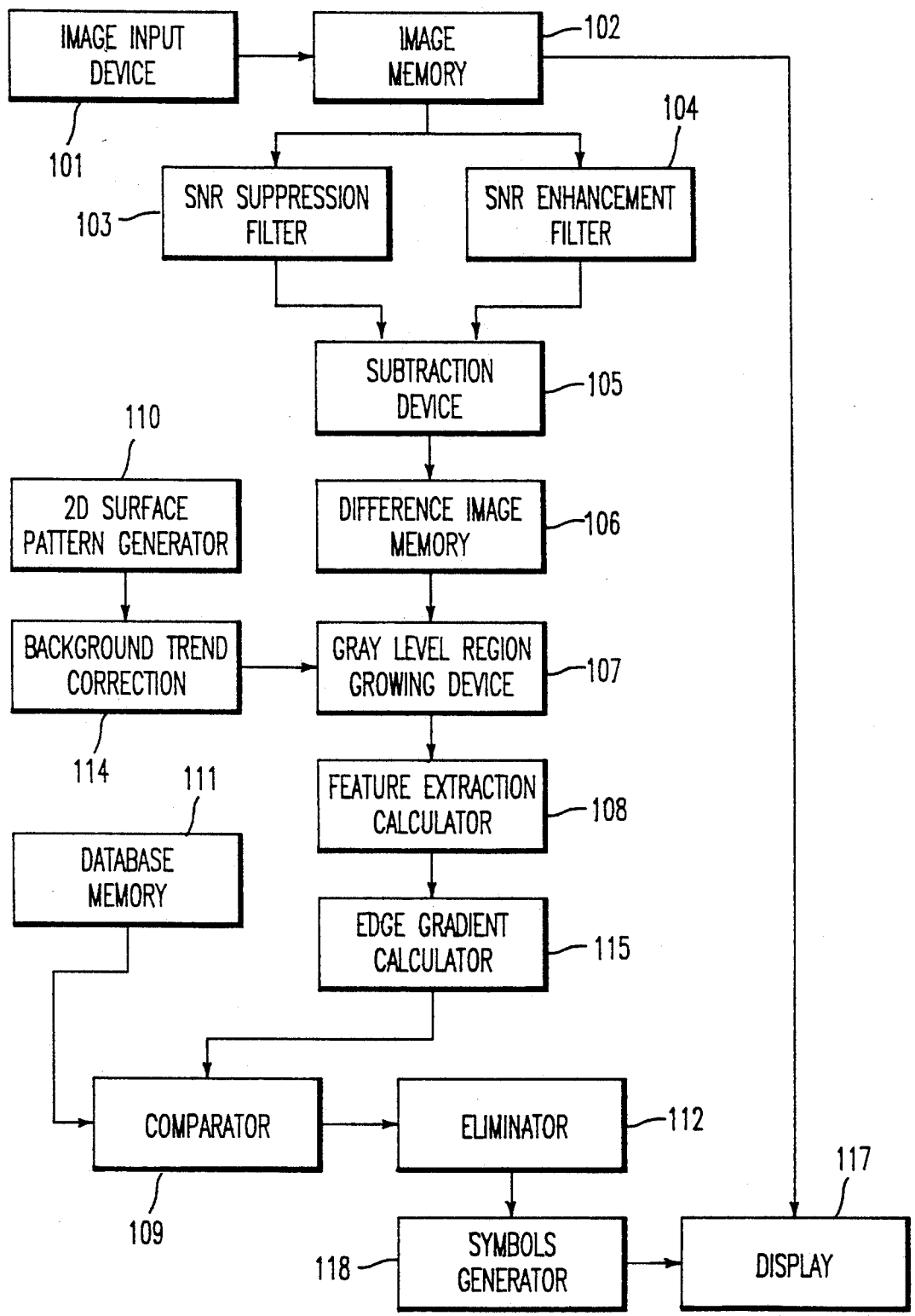
FIG. 2 shows the overall system used for implementing the overall scheme of the present invention.

FIG. 2 shows the corresponding system used to implement the false-positive candidate reduction scheme of the present invention. Initially, X-ray images are digitized and input into an image input device 101 and then applied to an image memory means 102 which stores the original image to be later output to a display means 117. The image memory 102 outputs the digitized image simultaneously to a SNR suppression filter 103 and a SNR enhancement filter 104. A subtraction device 105 then generates the difference image to be stored in memory 106. A gray-level region growing means 107, described in U.S. Pat. No. 4,907,156, receives the difference image in order to begin the region growing technique which will be described in more detail later. The parameter values of effective diameter and degree of circularity and irregularity are generated by feature extraction calculator 108 and these values are then subjected to edge gradient analysis calculations in edge gradient calculator 115 involving the generation of an edge gradient orientation histogram so as to analyze the magnitude of standard deviations for each edge gradient calculation performed on the selected ROIs containing nodule candidates. The amount of standard deviation for these individual ROIs will be used in determining if the nodule candidates contained therein are false-positives.

The various parameter values calculated (e.g., edge gradient standard deviations, degree of circularity, etc.) are then compared in comparator 109 with predetermined threshold values stored in database memory 111. These predetermined values were determined by analysis of the above described parameter values for known abnormalities (actual nodules) using expert analysis and more complicated procedures known in the field of nodule detection (e.g. CT scans, radiographic follow-up, etc.). Those nodule candidates which exhibit parameter values within ranges common only to false-positives are then eliminated in eliminator device 112. A symbols generator then outputs various symbols corresponding to the size, shape, severity, etc. of the nodule candidates that have not been eliminated so as to be superimposed on the original digitized image on display 117. It should be noted that for a first set of parameter calculations, the system of FIG. 2 is used with a background trend correction means 114 and corresponding two-dimensional surface pattern generator 110. The purpose of background trend correction here is to correct for underlying background trend images which may exist in the original digitized image. Background corrected profile data are obtained by subtracting a fitted background trend from the original profile data. This corrected image is then applied to gray level region growing device 107. In a second set of data, on the other hand, no background trend correction is used for reasons to be enumerated below.

In the present invention, 60 conventional, postero-anterior chest radiographs were used which were obtained from 30 normal cases and 30 abnormal cases, having 32 pulmonary nodules with diameters ranging from 6 mm to 25 mm. The presence of pulmonary nodules was verified by CT scans or radiographic follow-up. These methods have the disadvantages of being more complicated and costly, and thus the method and system of the present invention have been developed in order to overcome the drawbacks associated with these conventional methods. Calcified nodules and nodules with secondary features, such as atelectasis, were excluded. In the 30 normal cases, absence of nodules was confirmed by consensus of two chest radiologists.

In order to identify the features of false-positives, the relationships between the various measures for the 23 actual nodules and the 712 false-positives were analyzed, including false positives arising from various normal background structures.

The method and system of the present invention will now be described in greater detail with specific reference to FIGS. 3 through 14. The clinical chest radiographs used were digitized by an optical drum scanner with a 0.1 mm pixel size and 10-bit quantization. The images were subsequently averaged into a $512 \times 512$ matrix with an effective pixel size of 0.6 mm. Note that the pixel value (or gray value) of digitized images is approximately inversely proportional to the optical density of original radiographs, i.e., as the radiograph density increases, the number of pixels contained in a given area decreases. Digitized images were analyzed on a DEC VAX 3500 computer with the automated detection scheme.

Difference images were produced in order to reduce the camouflaging anatomic background in the chest image and thus enhance the conspicuity of nodules. The difference image was obtained from the subtraction of a "nodule-suppressed" image from a "nodule-enhanced" image. Each of these images was produced using linear filters that included a matched filter and a ring-shape averaging filter for enhancement and suppression, respectively. Three feature-extraction techniques were then applied to all computer-suspected densities in the difference image in order to reduce false-positive detections arising from normal anatomical background features, also known as "structured noise". In the present invention, the criteria for nodule detection was relaxed which resulted in a larger number of false-positive detections and a slightly higher sensitivity. Thus, the shadows detected with the relaxed criteria corresponded to nodule candidates that included 23 true nodules and 712 false positives. These candidates were analyzed using the VAX 3500 computer.

Gray-level region growing in the original image data was used as an initial step in the quantitative analysis of the nodule candidates. For each candidate nodule, the starting pixel for region growing was selected as the one having the highest gray level within a 15 pixel distance from the (x,y) location of the candidate, as identified previously in the difference-image. Then, region growing was performed for various gray-level intervals in increments of 3 pixel values. Once the starting pixel (x,y) is determined, the initial grown region is formed by the method of "fanning out" in all directions using a $3 \times 3$ pixel matrix to search around the original (x,y) data point in order to determine the outer boundaries of the initial grown region having a constant gray level value. Once this initial grown region is established, the next gray level interval outside the perimeter of the first grown region is analyzed in a similar manner in order to determine the next outer grown region, and this process continues for a selected number of grown regions to be formed. Such a gray level region growing process is well known in the art of image digitization and quantization.

Figure 4A:
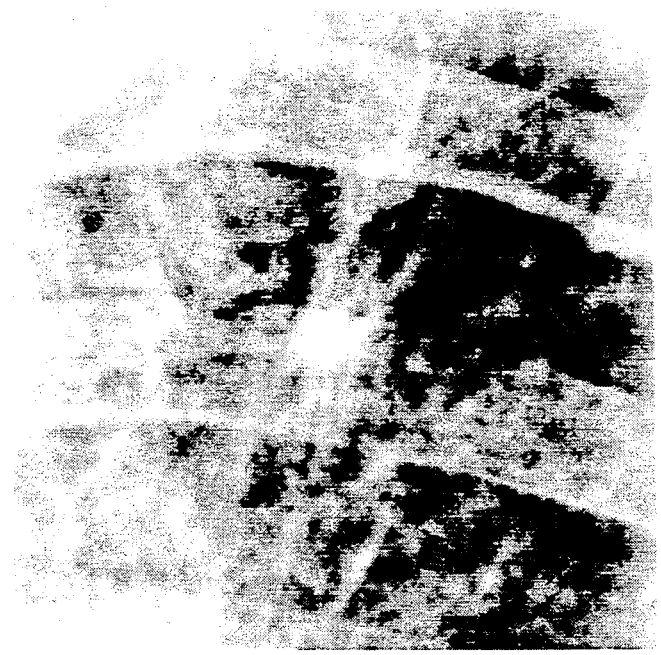
FIG. 4a shows an original digital image of an actual nodule (true-positive) case.
Figure 4B:
FIG. 4b illustrates the corresponding contour-line image of FIG. 4a magnified slightly.
Figure 5:
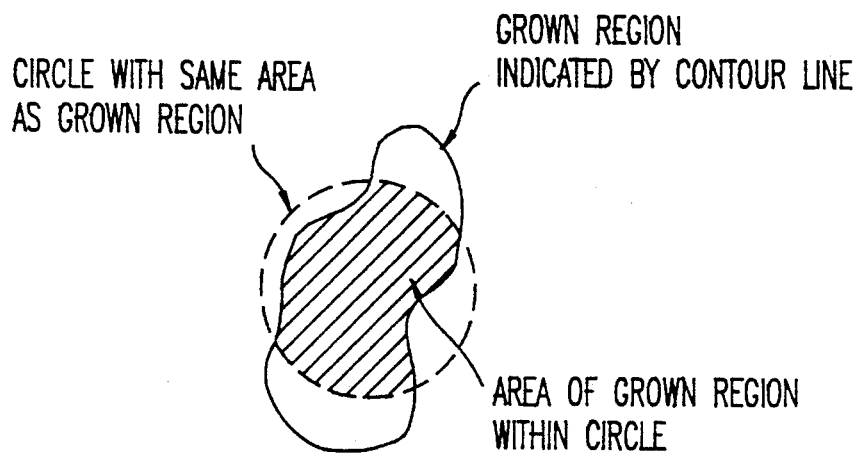
FIG. 5 is an illustration of definitions of the effective diameter, the degree of circularity, and the degree of irregularity of a grown region.

FIGS. 4a and 4b show a nodule and the corresponding contour lines, respectively; contour lines represent the grown areas for the various gray-level intervals. The gray level intervals are defined as the difference from one gray level region to another (e.g. adjacent) gray level region. The area within each contour line is defined as a grown region. Image features of each grown region were quantified by calculating the effective diameter, the degree of circularity and the degree of irregularity. These measures are defined in FIG. 5. The effective diameter and the degree of circularity for a grown region are defined in the same way as those for an island (i.e., nodule candidate) appearing in the difference image, see U.S. Pat. No. 4,907,156. The degree of irregularity of the nodule candidate is defined as one minus the ratio of the perimeter (circumference) of the circle having the same area as the nodule candidate to the length of the contour line (i.e., the perimeter of the grown region), as shown in FIG. 5. When the shape of the region enclosed by the contour line approaches that of a circle, the degree of irregularity becomes the minimum value of zero. On the other hand, when the shadow contains many large spicules (i.e., irregularities), the degree of irregularity may approach the maximum value of one. The contrast of the grown region is defined as the gray-level interval, used in the region-growing process, that yielded the grown region in question.

FIG. 4c shows the relationships between the three measures and the contrast of the grown regions for the nodule shown in FIG. 4b. The contrast and the other measures are plotted on the abscissa and ordinate, respectively. This diagram appears somewhat complex, but was found to be very useful for the understanding of the complicated variations of the features of a nodule candidate in a concise manner.

It should be noted from FIG. 4c that the effective diameter of the grown region increases abruptly from approximately 14 to 33 pixels at a contrast of 75. This transition indicates that the grown region has merged with the surrounding background adjacent to the nodule candidate. It should also be noted that similar transitions occur in the measures for circularity and irregularity. The grown region at the point just prior to this transition, as illustrated by the light area in FIG. 4b, appears to be very similar visually to the actual shape and size of the nodule candidate (FIG. 4a). This point prior to the transition will be called the transition point. Here the candidate contrast is also defined as the contrast of the grown region at the transition point. Although it is possible that the actual contrast of the nodule candidate may be represented by the contrast immediately after the transition occurred, the difference between these two contrasts is usually insignificant.

The gray areas in FIG. 4b correspond to those that resulted from region growing beyond the transition point. In order to examine the nature of the background structure adjacent to the nodule candidate, a "background" region is identified by a large square, whose size (area) is two times the effective diameter of the grown region at the transition point. The actual area of the grown region at the transition point is excluded from the calculated area of the square background region. In order to establish the centering arrangement of the background region around the outermost grown region, i.e., the grown region at the transition point, the centroid of the outermost grown region is determined using a known mathematical formula, i.e., to find the "weighted" center point of the grown region. The background region is then centered at this centroid point with the previously mentioned calculated area. A background contrast is then defined as the difference between the gray level contrast at the transition point and the average contrast of the background region.

Figure 6A:
FIG. 6a is an original digital image of an actual nodule (true-positive) case in the peripheral region of a lung.
Figure 6B:
FIG. 6b illustrates the contour-line image of FIG. 6a without trend-correction.
Figure 6C:
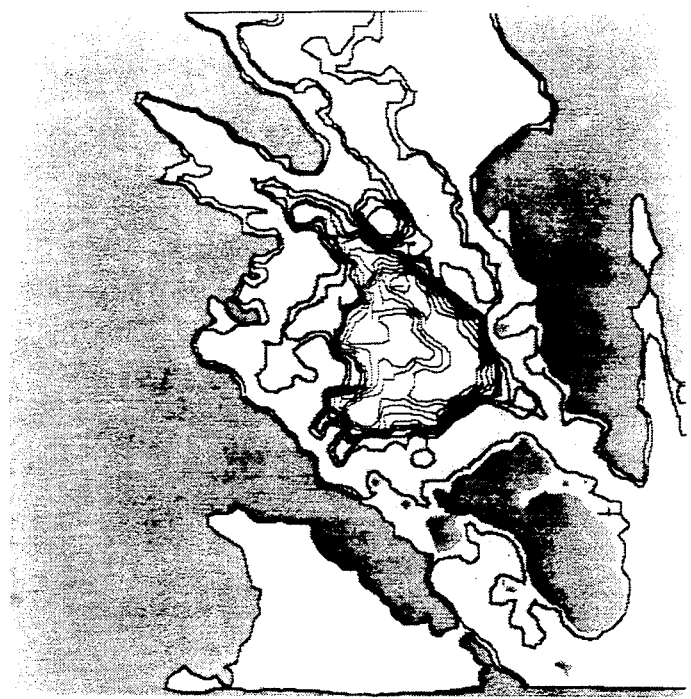
FIG. 6c shows the contour line image of FIG. 6a with trend-correction.

With some candidate nodules, however, either a transition point could not be found, or the shape of the grown region at the transition point appeared quite different from that of the nodule candidate in the original chest image as shown in FIGS. 6a and 6b. This especially occurred in peripheral regions. Such occurrences were due to the nonuniformity of the background density distribution. Therefore, a two-dimension background trend-correction technique was used, similar to that disclosed in U.S. Pat. No. 4,839,807 to Doi et al, incorporated herein by reference. With this technique, the transition points were able to be clearly identified, and the shapes and sizes of the grown regions at the transition points became similar to those of the nodule candidates in the chest images (see FIG. 6c) for almost all such nodule candidates.

Figure 7A:
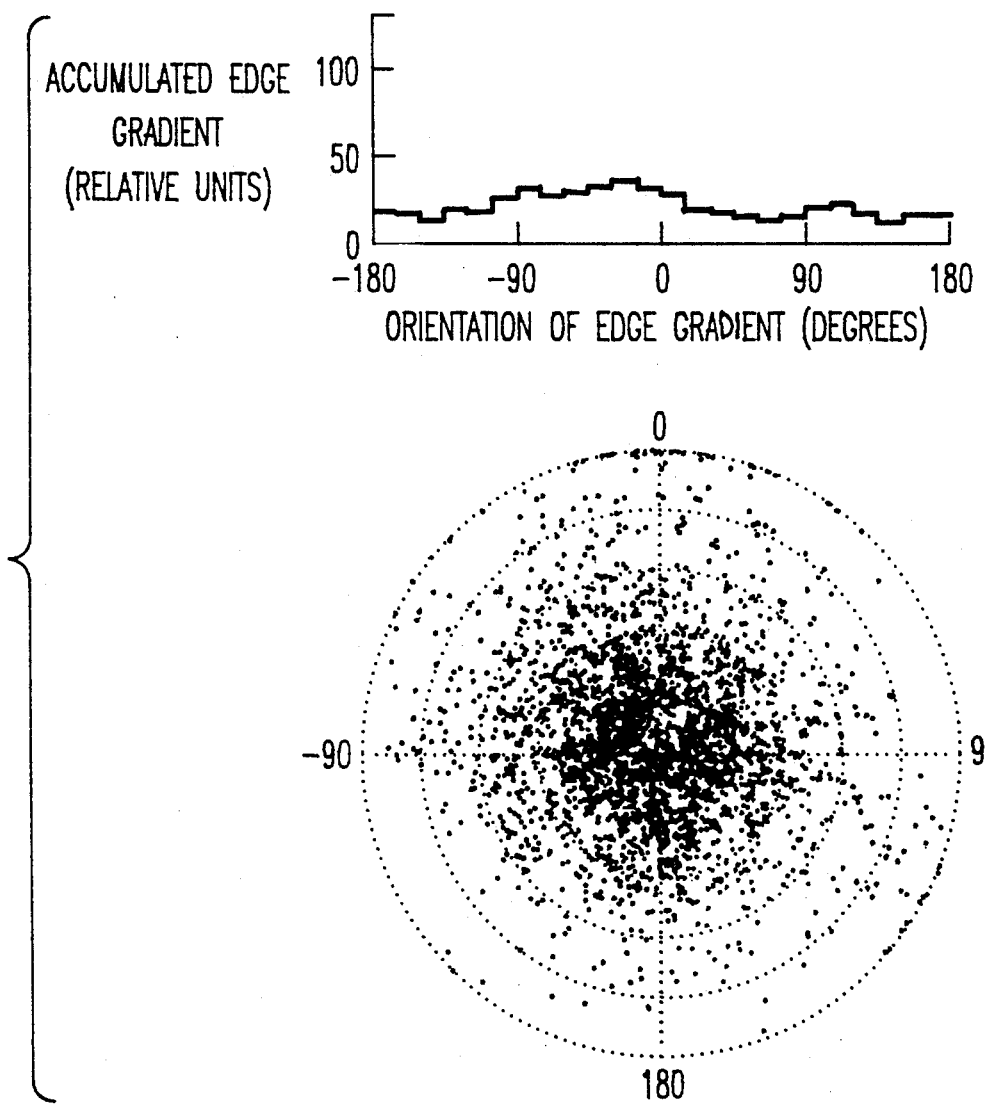
FIG. 7a shows gradient-orientation distributions (top), and the magnitude and orientation of edge gradients of FIG. 4a for pixels in 50×50 pixel ROIs (below)
Figure 7B:
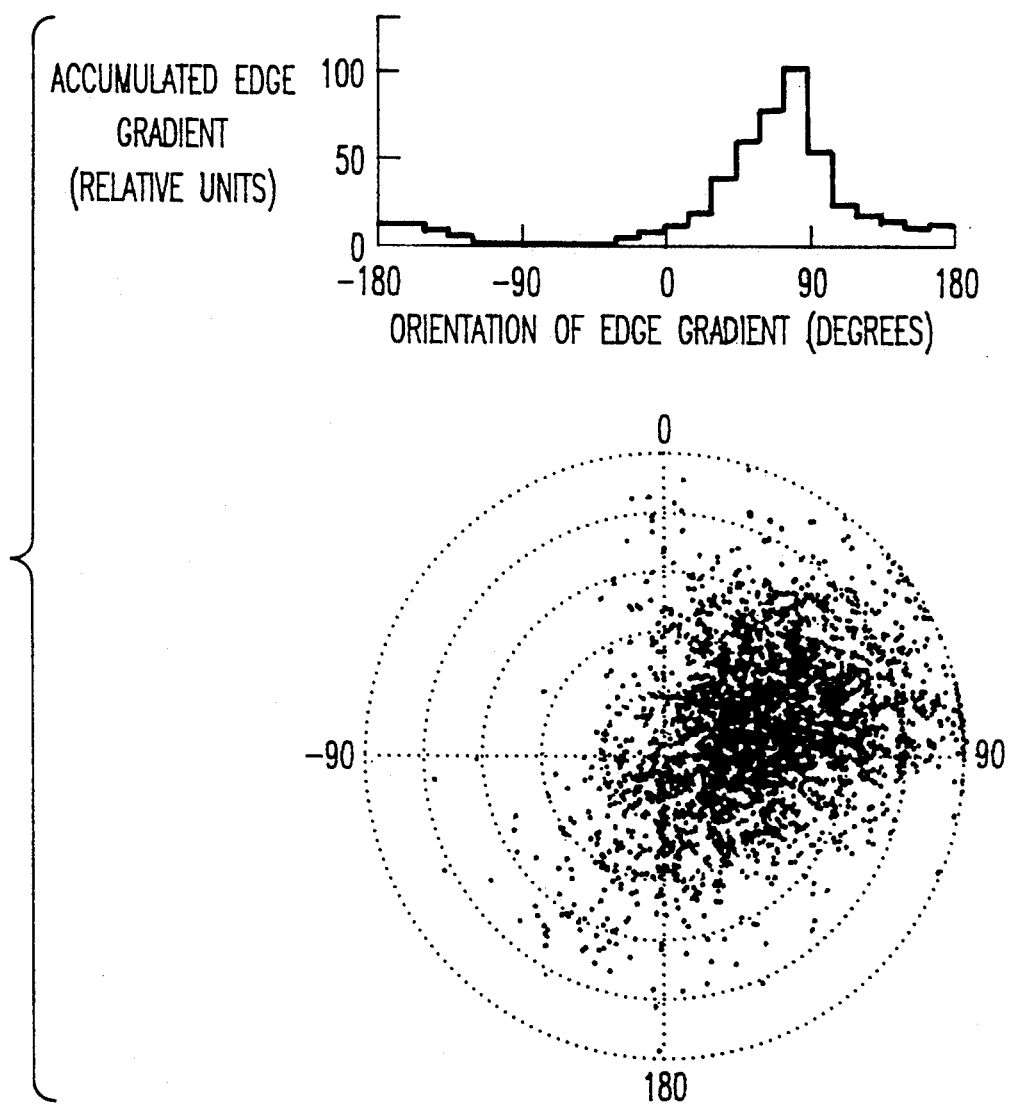
FIG. 7b shows gradient-orientation distributions (top), and the magnitude and orientation of edge gradients of FIG. 6a for pixels in 50×50 pixel ROIs (below)

In the present invention, a well known edge-gradient analysis technique is also used. For each candidate nodule, the magnitude and orientation of edge gradients were calculated for pixels within a 50 pixel by 50 pixel ROI (region of interest), centered at the same pixel location that was used previously for initializing the region growing process. FIGS. 7a and 7b show the plots of the magnitude and orientation of edge gradients for pixels in the ROIs about the candidate nodules of FIGS. 4a and 6a, respectively. Note that no background trend correction was performed on these ROIs. The top of FIGS. 7a and 7b illustrate the gradient-orientation distributions from which the averages and relative standard deviations of gradient-orientation distributions are calculated. For a ROI with a nodule and many vessels as shown in FIG. 4a, edge gradients are generally oriented in all directions. Therefore, its gradient-orientation distribution is relatively uniform with a relatively small standard deviation as illustrated in FIG. 7a. However, for ROIs such as that shown in FIG. 6a, in which a rib edge overlaps with the border of the nodule, the gradient-orientation distribution shows a definite directionality and the relative standard deviation of the gradient-orientation distribution is usually large as shown in FIG. 7b. The average gradient and the relative standard deviation of the gradient-orientation distribution of FIG. 7a are 75.3 and 33.0%, respectively, and those of FIG. 7b are 93.6 and 131.2%, respectively. The relative standard deviation is normalized by the average gradient.

Although true nodules generally contained high circularity, some true nodules, when partially overlapped with a rib, contained low circularity. This is because the pixel values of an area of a nodule overlapped with a rib are quite different from those of the area of the nodule without overlap. Thus the shape of the grown region at the transition point, based on the region-growing technique, is often different from the appearance of true nodules. This condition can be detected by the existence of a strong directional dependence in the edge-gradient orientation distribution. On the other hand, when a strong directional dependence is absent, the grown region is similar to the appearance of an actual nodule. Therefore, in areas with a small standard deviation of the gradient-orientation distribution, the degree of circularity of true nodules tends to be higher than those of some false-positives.

Figure 8:
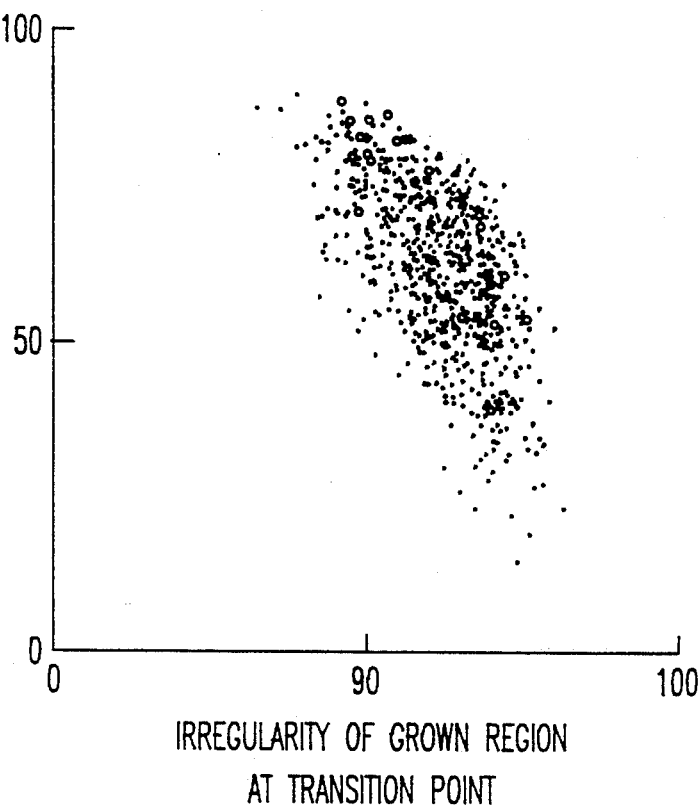
FIG. 8 illustrates the relationship between the degree of circularity and the degree of irregularity of grown regions at the transition point for trend-corrected areas of candidate nodules, (o: actual nodule; dot: false positive)

FIG. 8 shows the relationship between the degree of circularity and the degree of irregularity at the transition point for trend-corrected candidate-nodule images. Some false-positives (approximately 20% of all false-positives) exhibited both low circularity (below 63%)

and low irregularity (below 65%). It can be predicted, therefore, that the shapes of nodule candidates in this group are quite different from a circle and are more similar to a triangle or a square. However, some actual nodules may exhibit low circularity when they contain many large spicules. In addition, it was found that when actual nodules exhibit low irregularity, they tend to demonstrate high circularity also. However, an actual nodule seldom exhibits low circularity and low irregularity. Therefore, a nodule candidate with low circularity and low irregularity is likely to be a false-positive.

Figure 9:
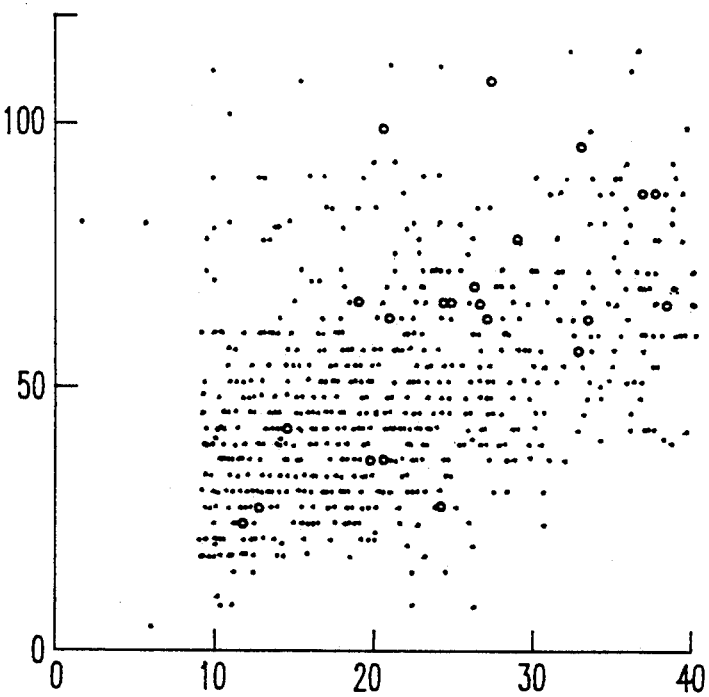
FIG. 9 illustrates the relationship between the effective diameter of grown regions at the transition point and candidate contrast for trend-corrected areas, (o: actual nodule; dot: false positive)

FIG. 9 shows the relationship between the effective diameter and the contrast of the nodule candidates at the transition point. It is apparent in FIG. 9 that some false-positives (approximately 5%) exhibited low candidate contrast (below 45 gray levels) with a large size (more than 25 pixels) in the trend-corrected regions. In addition, nodule candidates (approximately 18%) with high candidate contrast (more than 45 gray levels) with a small size (below 19 pixels) in the trend-corrected image were also considered false-positives, because calcified nodules were excluded from our database.

Next, the features of the various important false-positives were analyzed. These false-positives had been identified as major sources of computer error in the automated detection of lung nodules in the prior art method and system disclosed in U.S. Pat. No. 4,907,156.

AGGREGATE OF VESSELS

Figure 10A:
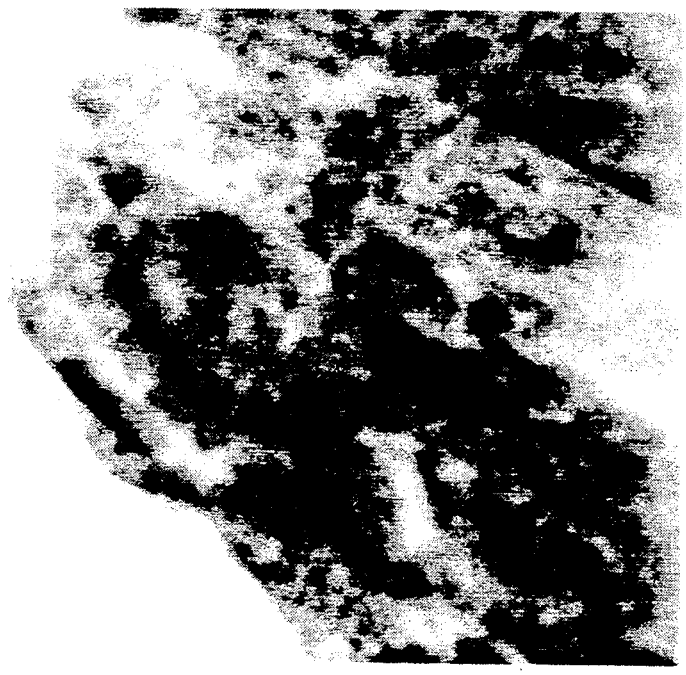
FIG. 10a shows the original digital image of a false-positive case due to an aggregate of vessels.
Figure 10C:
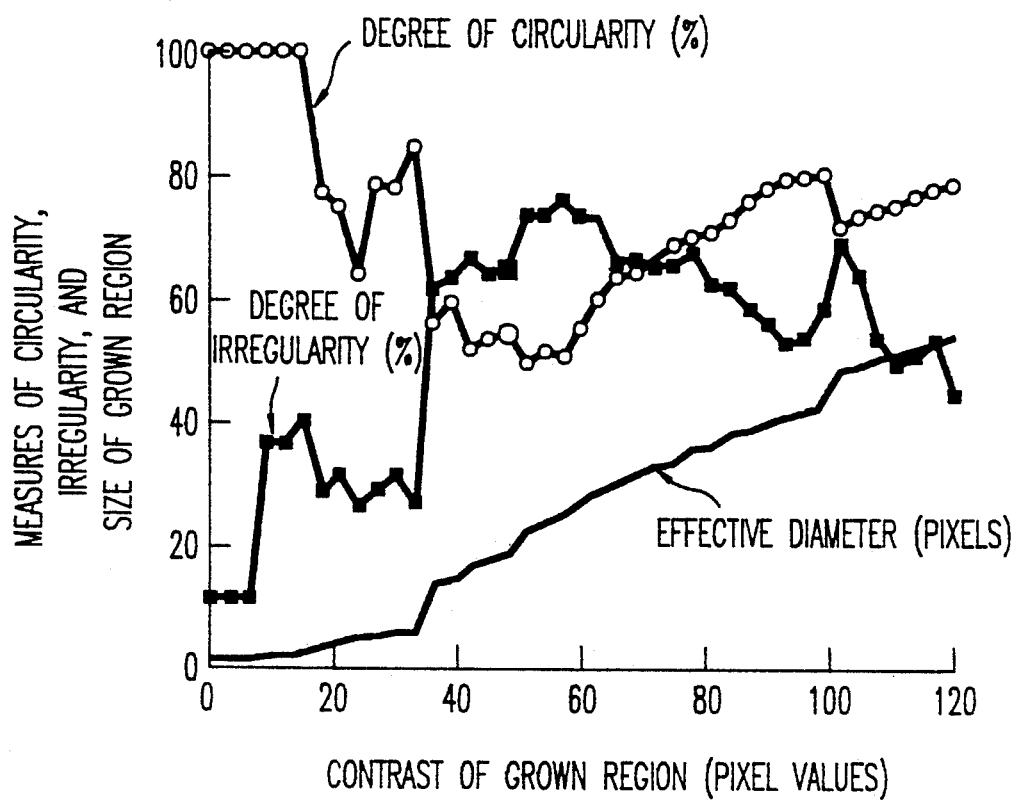
FIG. 10c illustrates the relationship between the contrast and the measures of circularity, irregularity and size of grown regions.
Figure 10D:
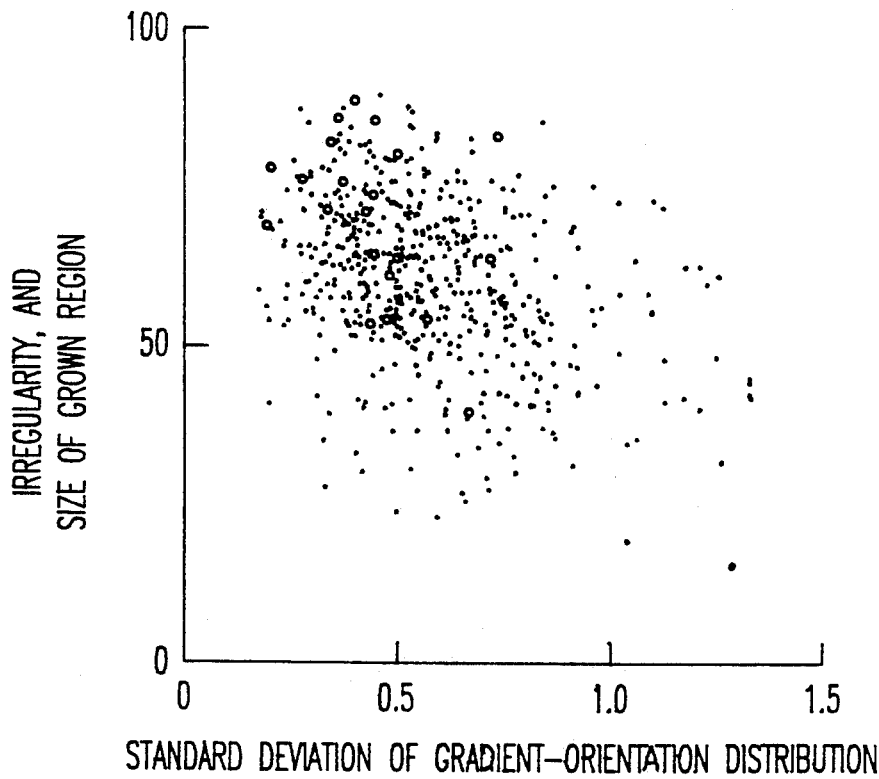
FIG. 10d illustrates the relationship between the degree of circularity at the transition point and the relative standard deviation of the gradient-orientation distributions of nodule candidates.

In general, when aggregated vessels are detected as false-positives, many of the vessels are, relatively large and are oriented in various directions, as can be seen from FIG. 10a. These shadows of aggregated vessels are usually located in the hilar or perihilar regions, and tend to have irregular margins and a non-circular shape. Because of the relatively large size of the vessels involved, the average gradient is usually high and the relative standard deviation of the gradient-orientation distribution is small since the vessels can be oriented in various directions as indicated in FIG. 10b. If no nodule is present in an area having such characteristics, the circularity is commonly low and the irregularity is high as shown in FIG. 10c. On the other hand, when a nodule is present, the circularity is generally high. Thus, the relationship between the degree of circularity at the transition point and the relative standard deviation of the gradient-orientation distribution can be used to identify these potential false-positives whose average gradients are greater than 50. As shown in FIG. 10d, some false-positives (approximately 5%) that had small standard deviations (below 0.4) of the gradient-orientation distribution exhibited low circularity (below 60%) compared with those of true nodules in the trend-corrected regions. Average gradient and relative standard deviation of the gradient-orientation distribution of this region are 91.0 and 39.7%, respectively. Note that only nodule candidates with average gradient greater than 50 are plotted in FIG. 10d.

RIB-RIB (OR CLAVICLE) CROSSING

Figure 11A:
FIG. 11a shows a false-positive candidate due to a rib-clavicle crossing.
Figure 11B:
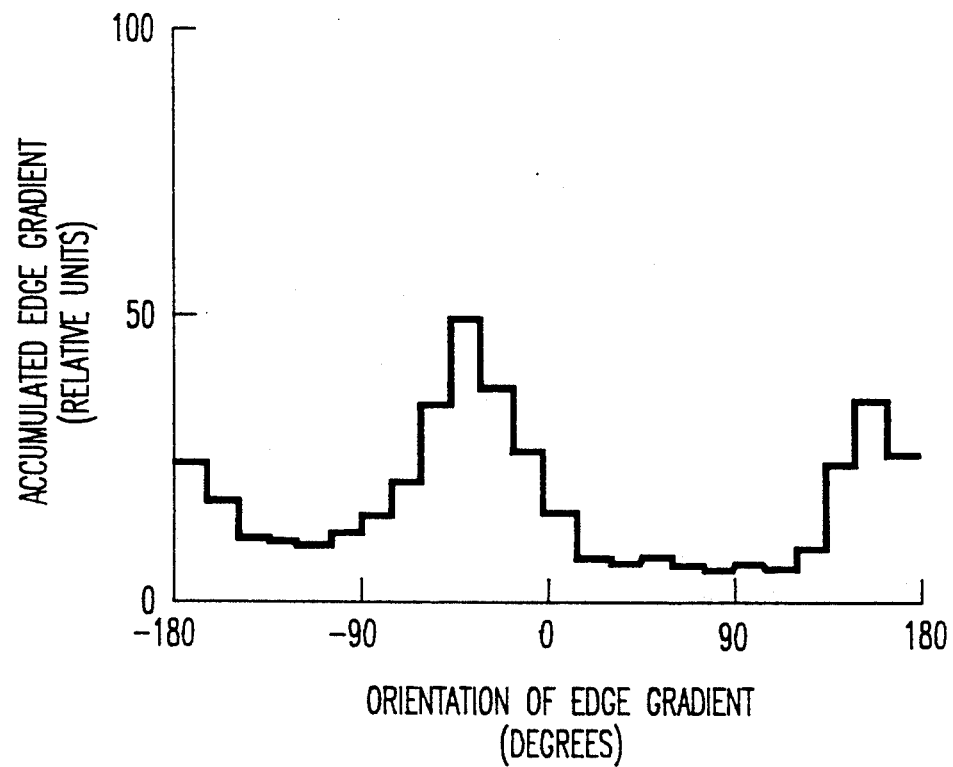
Figure 11C:
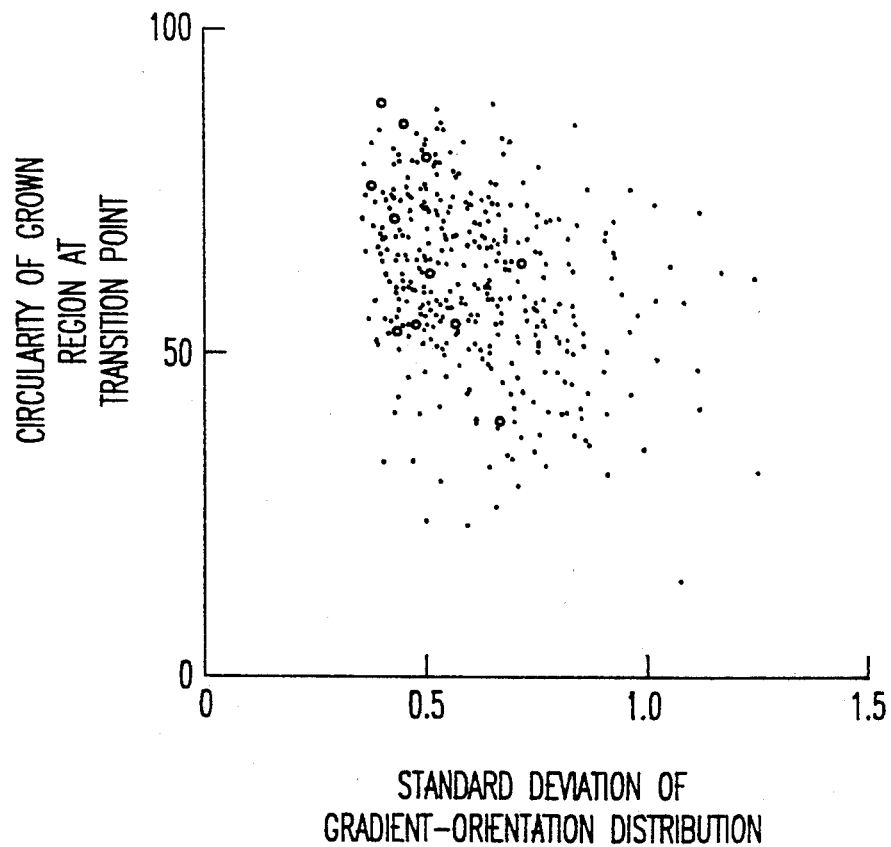
FIG. 11c illustrates the relationship between standard deviation of the gradient-orientation distribution and degree of circularity at the transition point for the database.

The unique feature of rib-rib or rib-clavicle crossings is that two or more lines (or edges) are present, but no convex margins are detected, as can be seen from FIG. 11a. If two obvious lines are present in the original image, two narrow peaks at an approximately 180 degree separation can be identified in the gradient-orientation distribution, and the standard deviation of the distribution is relatively large, as is apparent from FIG. 11b. For true nodules, however, even if superimposed on a rib, the relative standard deviation of the gradient-orientation distribution has a moderate value, because its shadow will include various edge-gradients in all directions due to the margin of the nodule and also some edge gradients in particular directions due to the presence of ribs. Therefore, the relationship between the degree of circularity at the transition point and the relative standard deviation of the gradient-orientation distribution can again be used to identify potential false positives. As shown in FIG. 11c, some false-positives (approximately 12%) having two narrow peaks separated by approximately 180 degrees had large standard deviations for the gradient-orientation distribution (more than 0.75) compared with those of true nodules in the trend-corrected regions. Average gradient and relative standard deviation of the gradient-orientation distribution for this case are 67.5 and 111.8%, respectively. Note that only nodule candidates with two narrow peaks at approximately 180 degree separation are plotted in FIG. 11c.

RIB-VESSEL CROSSING

Since a 9-mm matched-filter was used for enhancement, very small shadows were not detected as nodule candidates in the difference image. To be detected as a candidate in the difference image, the size of both a rib edge and vessel needs to be comparable to or larger than the size of the matched filter kernal. This suggests that relatively large vessels might be detected as false positives. Therefore, the false-positives located at a rib-vessel crossing (or a vessel-vessel crossing) would be present in a hilar or perihilar region, and would exhibit band shadows crossing in the original image. In the case of a relatively large vessel and a rib edge crossing, this shadow has relatively high candidate contrast.

Figure 12A:
FIG. 12a shows an example of a false-positive candidate due to a rib-vessel crossing.
Figure 12B:
Figure 12C:
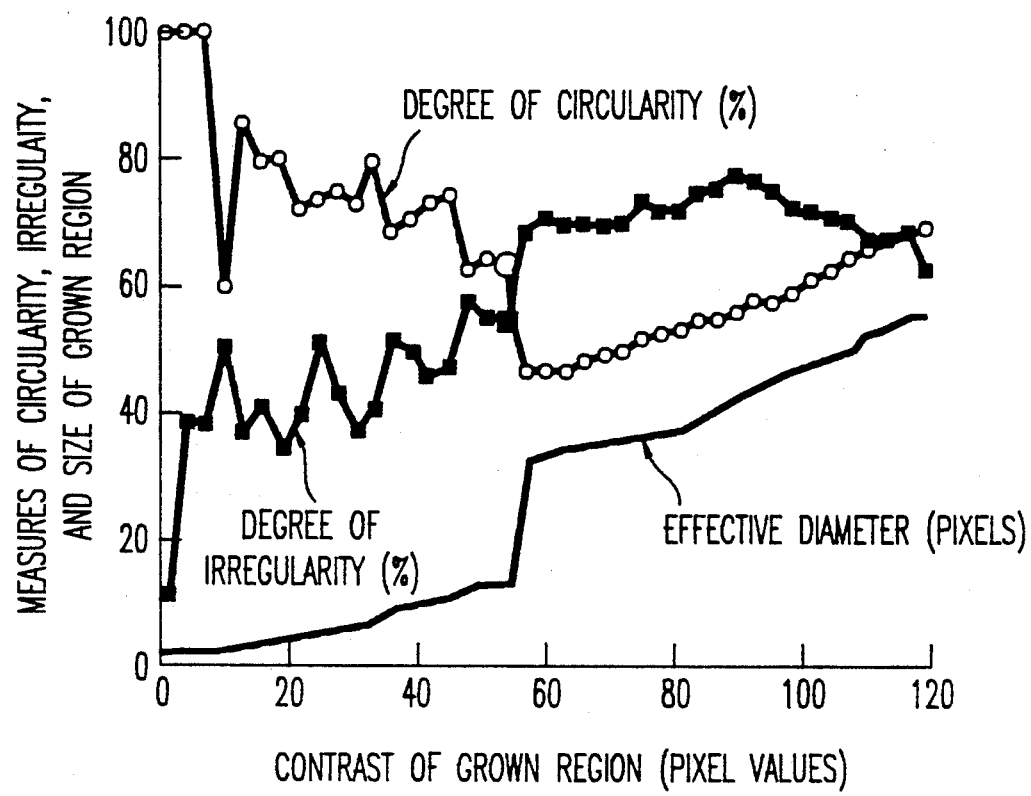
FIG. 12c illustrates the relationship between the measures of circularity, irregularity, effective diameter, and contrast of the grown region for the nodule candidate.
Figure 12D:
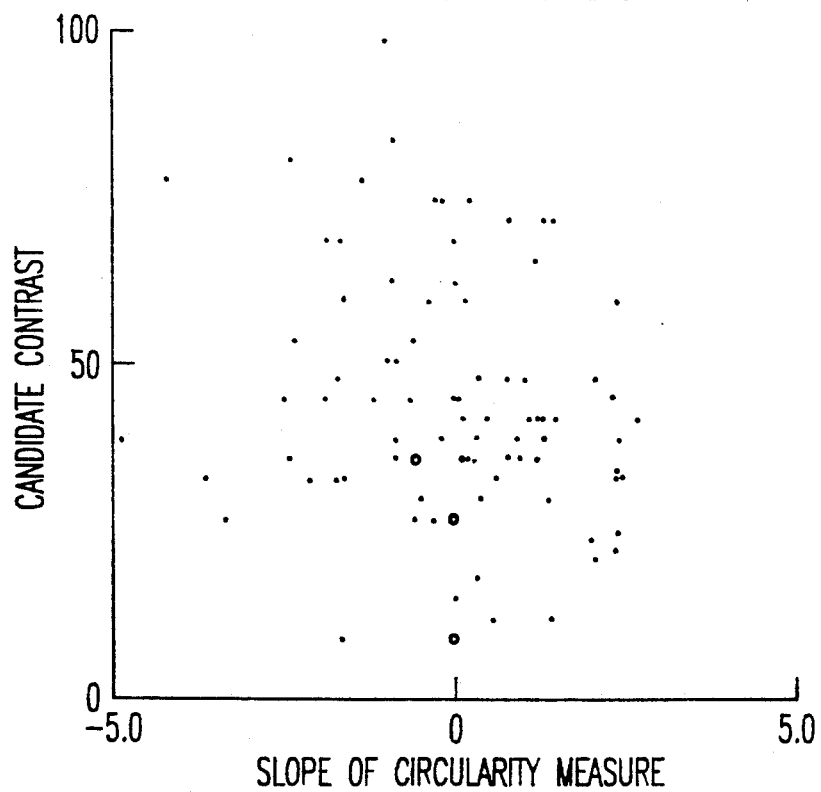
FIG. 12d illustrates the relationship between the slope of the circularity measure and the candidate contrast for nodule candidates.

Note that a vessel is cylindrical, and that when the vessel is projected longitudinally, pixel values at the center of the vessel are greater than those at the borders. Therefore, when a vessel and rib edge cross, the circularity and the irregularity of the small grown region tend to be high and low, respectively, at the center of crossing, as shown in FIGS. 12a and 12b. As the size of the grown region increases, however, the circularity gradually decreases and the irregularity gradually increases up to the transition point, see FIG. 12c. FIG. 12d shows the relationship between the slope of the circularity measure and the candidate contrast for true nodules and false-positives which exhibited positive slopes of irregularity and low circularity (less than 80%) measures at their transition points. The slopes of circularity and irregularity refer to the instantaneous slopes at or around selected candidate values, i.e., in FIG. 12c the slope of irregularity from zero to three contrast pixel values is positive. Transition points in these images are found without trend-correction. Some false-positives (approximately 3%) contained this feature. Note that the candidates with the degree of circularity below 80% and slope of irregularity greater than zero are plotted in FIG. 12d.

END-ON VESSELS

Figure 13A:
FIG. 13a shows an example of a false-positive candidate due to an end-on vessel.
Figure 13B:
Figure 13C:
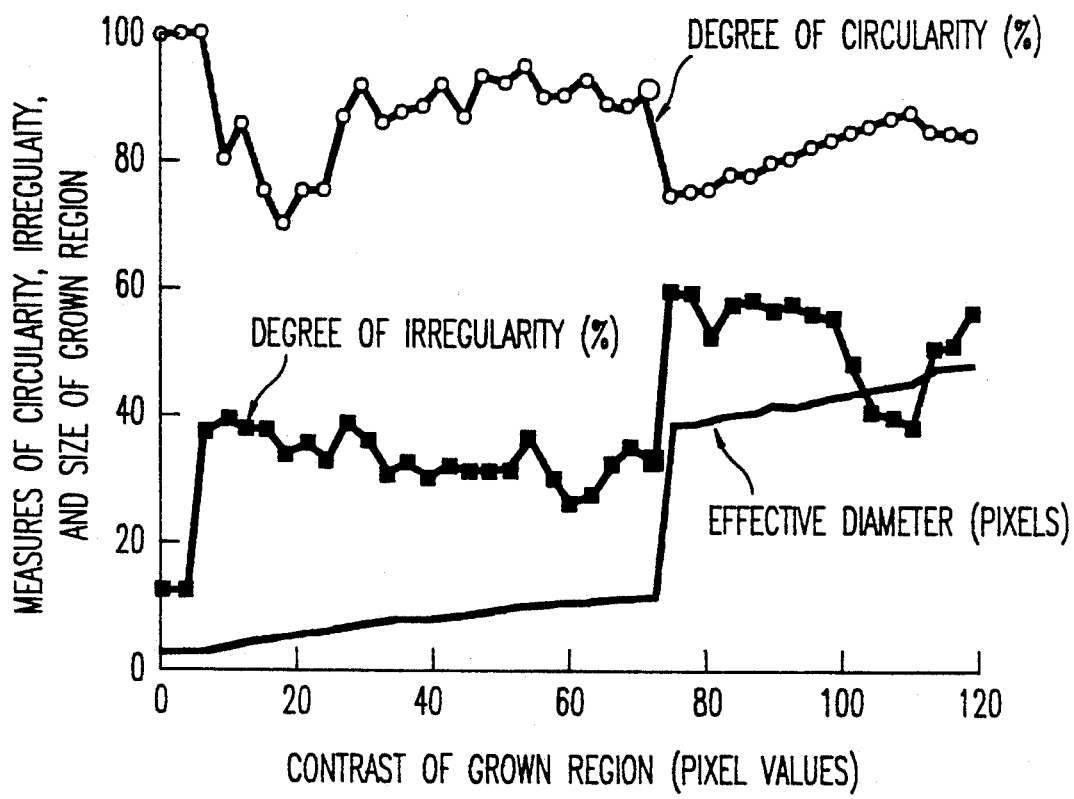
FIG. 13c illustrates the relationship between the measures of circularity, irregularity, effective diameter and the contrast of the grown region for the nodule candidate.
Figure 13D:
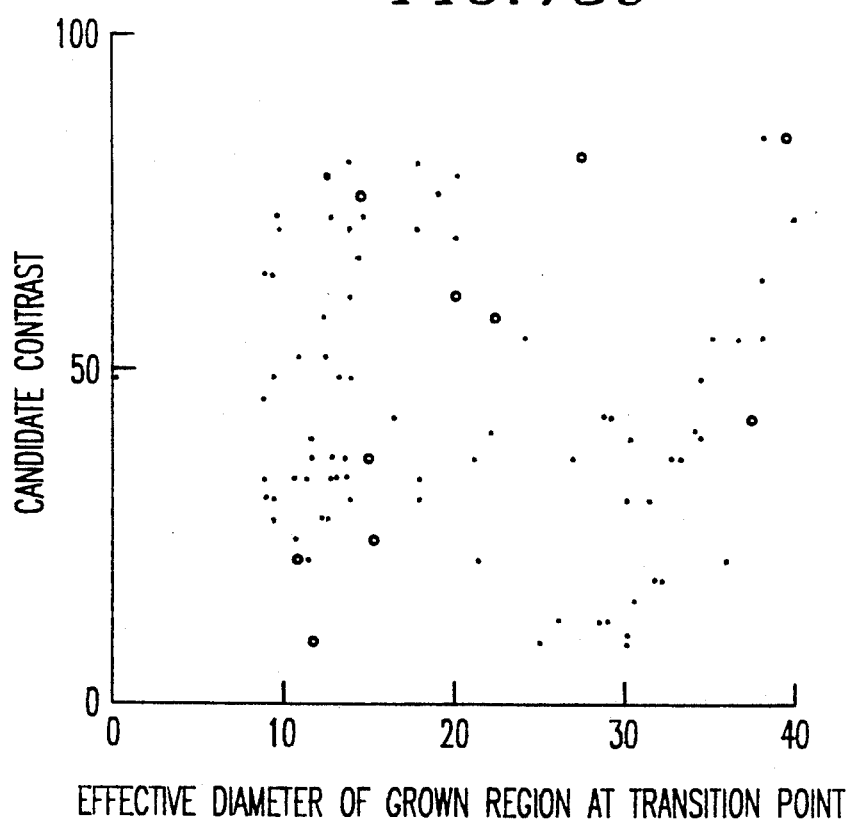
FIG. 13d illustrates the relationship between the candidate contrast and effective diameter of grown regions at the transition point.

Since the shadow of an end-on vessel is formed by the incident x-ray beam parallel to the vessel, the shape of its shadow may be characterized generally by a small round pattern. Therefore, if a small nodule candidate in the hilar or perihilar region contains high contrast with a high degree of circularity, as in FIGS. 13a–13c, the candidate is likely to be a false-positive due to an end-on vessel. A small densely calcified nodule would produce a similar pattern, but since dense calcification indicates benignity, such nodules can be ignored. In order to analyze candidates with these characteristics, the relationship between candidate contrast and effective diameter of grown regions was examined at the transition point for nodule candidates with high circularity (more than 70%) as shown in FIG. 13d; the transition points in these images were determined without trend-correction. Some false-positives (approximately 4%) with high circularity, which are considered to be end-on vessels, had moderate effective diameters (9-12 pixels) and contained high candidate contrast (greater than 30 gray levels). Note that nodule candidates with high circularity (more than 70%) are plotted.

LOW-FREQUENCY ARTIFACTS

Some false-positives correspond to artifacts generated by filtering operations involved in the difference-image technique. These artifacts are usually located in extremely low-frequency structures such as a diaphragm or cardiac shadow and also adjacent to edges between those structures and the lung field. Because of the large difference in pixel values of large areas in the two sides of the edge, the background contrast is usually high. On the other hand, the pixel values inside the grown region are almost uniform. Therefore, the candidate contrast is relatively low.

Figure 14:
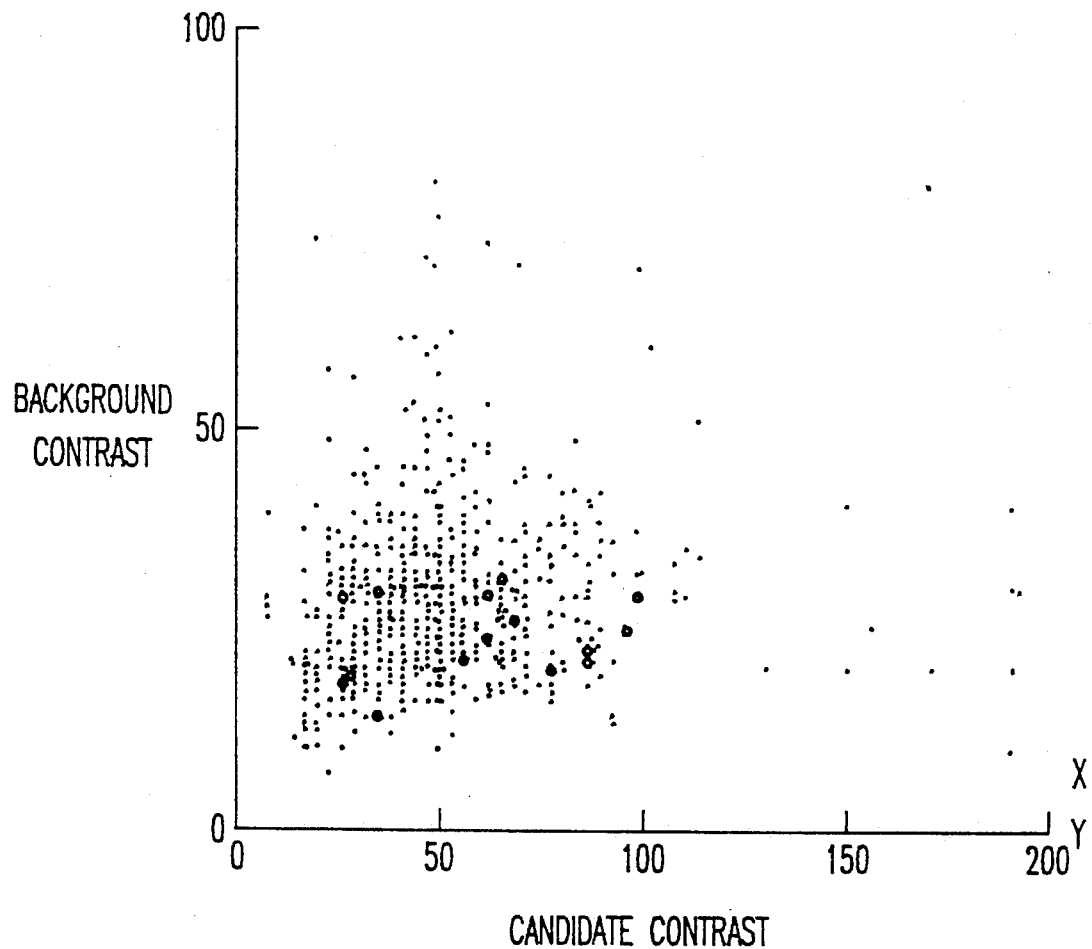
FIG. 14 shows a graph illustrating the relationship between the background contrast and the candidate contrast for low frequency artifacts.

FIG. 14 shows the relationship between the candidate contrast and the background contrast for true nodules and false-positives. Some false-positives (approximately 8%) had both high background contrast (greater than 32 gray levels), and low candidate contrast (below 40 gray levels), which can be identified as low-frequency artifacts. Using this information, additional false-positives due to these low-frequency artifacts can be eliminated based on the analysis of the relationship between the candidate contrast and the background contrast.

ELIMINATION OF FALSE-POSITIVES

Those nodule candidates that exhibited image features associated with the types of false positives described above were eliminated by examining the measures with respect to the threshold levels (cutoffs) obtained for each relationship. In addition, the nodule candidates, whose transition points were not detected (approximately 2%) were eliminated, and also those which had very low values for circularity (approximately 4% eliminated), irregularity (approximately 4% eliminated) or background contrast (approximately 3% eliminated) in trend-corrected regions.

Figure 3:
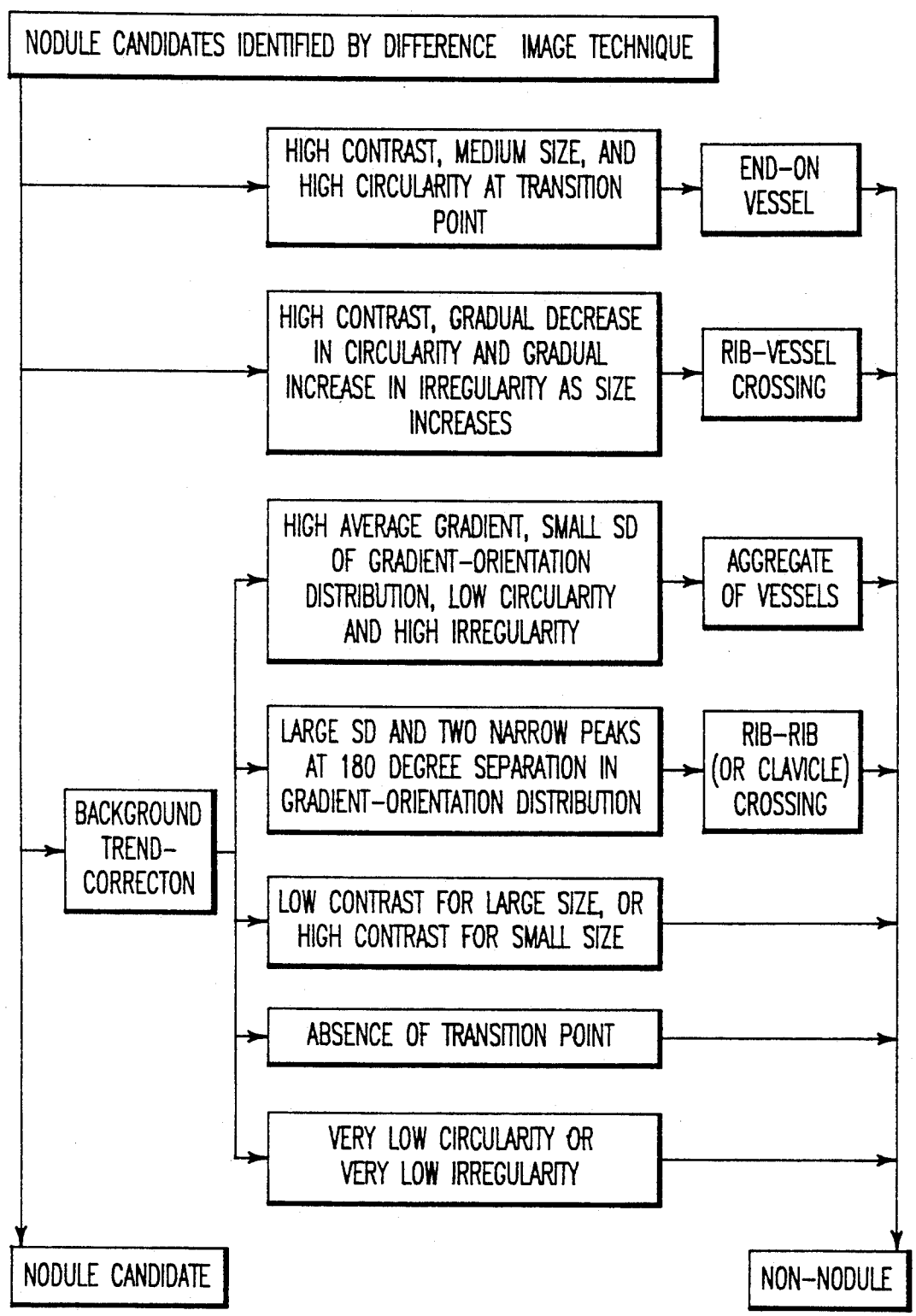
FIG. 3 shows a schematic diagram summarizing the criteria for reducing false positives.

FIG. 3 shows a summarized scheme for reducing the number of false-positives based on the methods described above. By using this scheme on our database with cut-off levels as described above, the average number of false-positives was able to be decreased from approximately twelve to approximately five per image without a reduction in detected true nodules (sensitivity: 71.9%).

When the prior art computer scheme of U.S. Pat. No. 4,907,156 was applied to 198 photofluorographic images obtained from a lung cancer screening program, the computer output was adjusted to a sensitivity level comparable to that of the trained human observers (approximately 60%), and the computer was able to detect 40% of nodules missed by human observers. Because the aim of this computer scheme is to alert radiologists to locations of possible nodules as a "second opinion", this result seemed to be favorable. However, the number of false-positives was unacceptably high. The locations of false-positives obtained with the computer scheme of the prior art were analyzed using the linear filtering method. The locations of these false-positives were quite different from those obtained by radiologists, and therefore it is believed that these false positives can be easily distinguished from true nodules in the original image through visual inspection by radiologists. Therefore, in order to eliminate the false-positives by computer, the present invention involves the analysis of the image features of false-positives based on the knowledge of trained observers. Various parameters have been defined and various methods employed in the computer scheme to utilize the knowledge of the human observers.

False-positives obtained with the previous computer scheme included various image features at various locations. For two types of false-positives arising from end-on vessels and rib-vessel crossings, the trend-correction technique was not used. These false-positives occurred near the mediastinum, where trend-correction would not be required; trend correction was necessary in peripheral regions. Another reason for not using the trend-correction technique is related to the findings that these false-positives usually have higher contrast and more homogeneous structure than true nodules; these false positives tend to have some unique features in the high contrast areas. If the trend-correction technique would be employed, the difference in pixel values between the mediastinum and small structures, such as vessels, would become large. Therefore, the transition point could be shifted incorrectly toward the further point which would become the margin of the another vessel adjacent to the end-on vessel or rib-vessel crossing in question. However, the images without the trend-correction, which can indicate the image features in high contrast areas, were useful for distinction between true nodules and these false-positives.

As mentioned above, false-positives obtained with the prior art computer scheme included various anatomic structures at various locations. It is apparent from the present invention that region growing, trend-correction and edge-gradient analyses can be useful in examining the characteristics of nodule candidates. Image features of many false-positives can be well represented by plotting the relationships between various measures, and can be confirmed by the knowledge of trained human observers.

Thus, in the present invention, the number of false-positives incurred in detecting lung nodules in digital chest images was reduced from approximately twelve to approximately five per image without a reduction in the sensitivity. This was achieved by incorporating a number of image features, which were derived from careful analysis of radiographic images by human observers, into the computer scheme. The present invention involves the continuing improvement of such computer detection schemes to the level where the sensitivity and the specificity are acceptable for clinical applications. The above results show that methods utilizing the knowledge of human observers can have an important role in improving the accuracy of computer schemes.

It should also be noted that the method and system of the present invention is not to be construed as being limited to pulmonary and mammography applications, but rather can be used in other medical situations such as magnetic resonance imaging techniques (MRI), CT scans, ultrasound images, bone radiography, etc.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for reducing the number of false-positive detections in a computerized scheme for detecting true-positive abnormalities on chest radiographs, comprising the steps of:

(a) storing a plurality of predetermined threshold values in memory, wherein said plurality of predetermined threshold values are characteristics of known false-positives related to average edge-gradient, edge-gradient distribution, standard deviation of edge-gradient orientation, transition point information, size, circularity, shape irregularity and contrast values;

(b) generating a digital image of an object;

(c) subjecting said digital image to a signal-to-noise ratio (SNR) enhancement filtering process and an SNR suppressed filtering process in order to produce respective first and second filtered digital images;

(d) obtaining a difference image by subtracting said second filtered digital image from said first filtered digital image, thereby enhancing the conspicuity of abnormality candidates included on said difference image;

(e) detecting the locations of said abnormality candidates included on said difference image;

(f) calculating a first set of parameters related to size, circularity, shape irregularity, edge-gradient, and contrast values for each abnormality candidate detected on said difference image;

(g) eliminating abnormality candidates having said first set of parameters related to size, circularity, shape irregularity, edge-gradient and contrast values within predetermined value ranges corresponding to a first set of said plurality of predetermined threshold values stored in memory;

(h) performing background trend correction on said digital difference image for the abnormality candidates remaining after elimination of said abnormality candidates in step (g);

(i) calculating, for each remaining abnormality candidate, a second set of parameters related to size, circularity, shape irregularity, edge-gradient and transition point; and (j) eliminating, as false-positives, said remaining abnormality candidates which have at least one of said parameter values calculated in step (i) within a predetermined value range corresponding to a second set of said plurality of predetermined threshold values stored in memory, thus providing an indication of the locations of said true-positive abnormalities on said chest radiographs.

2. The method for reducing the number of false-positive detections in a computerized scheme according to claim 1, wherein step (j) includes eliminating, as false-positives, said remaining abnormality candidates which have an average edge-gradient parameter above a first predetermined threshold, a standard deviation of edge-gradient orientation parameter less than a second predetermined threshold value, a circularity value less than a third predetermined threshold value and a shape irregularity value greater than a fourth predetermined threshold value.

3. The method for reducing the number of false-positive detections in a computerized scheme according to claim 1, wherein step (j) includes eliminating, as false-positives, remaining abnormality candidates with a standard deviation of edge-gradient orientation parameter greater than a fifth predetermined threshold value and having two narrow peaks at a 180° separation on said edge-gradient orientation distribution.

4. The method for reducing the number of false-positive detections in a computerized scheme according to claim 1, wherein step (j) includes eliminating, as false-positives, remaining abnormality candidates with a contrast value less than a sixth predetermined threshold value, a size greater than a seventh predetermined threshold value, or a contrast value greater than an eighth predetermined threshold value with a size less than a ninth predetermined threshold value.

5. The method for reducing the number of false-positive detections in a computerized scheme according to claim 1, wherein step (j) includes eliminating, as false-positives, remaining abnormality candidates for which a transition point is not found.

6. The method for reducing the number of false-positive detections in a computerized scheme according to claim 1, wherein step (j) includes eliminating, as false-positives, remaining abnormality candidates with a circularity value less than a tenth predetermined threshold value or a shape irregularity less than an eleventh predetermined threshold value.

7. A system for reducing the number of false-positive detections in a computerized scheme for detecting true-positive abnormalities on chest radiographs, comprising:

means for storing a plurality of predetermined threshold values, wherein said threshold values are characteristics of known false-positives related to average edge-gradient, edge-gradient distribution, standard deviation of edge-gradient orientation, transition point information, size, circularity, shape irregularity and contrast values;

means for generating a digital image of an object;

means for subjecting said digital image to a signal-to-noise ratio (SNR) enhancement filtering process and a signal-to-noise (SNR) suppressed filtering process in order to produce respective first and second filtered digital images;

means for obtaining a difference image by subtracting said second filtered digital image from said first filtered digital image, thereby enhancing the conspicuity of abnormality candidates included on said difference image;

means for calculating a first set of parameters related to size, circularity, shape irregularity, edge-gradient and contrast values for each abnormality candidate;

means for eliminating abnormality candidates having said first set of parameters related to size, circularity, shape irregularity, edge-gradient and contrast values within predetermined value ranges corresponding to a first set of said plurality of predetermined threshold values stored in memory;

means for performing background trend correction on said digital difference image for the abnormality candidates remaining after elimination of said abnormality candidates having size, circularity, shape irregularity, edge-gradient and contrast parameters within said predetermined value ranges;

means for calculating, for each remaining abnormality candidate, a second set of parameters related to size, circularity, shape irregularity, edge-gradient and transition point; and means for eliminating, as false-positives, said remaining abnormality candidates which have at least one of said second set of parameters within a predetermined value range corresponding to a second set of said plurality of predetermined threshold values stored in memory, thus providing an indication of the locations of said true-positive abnormalities on said chest radiographs.

8. The system according to claim 7, wherein said means for eliminating, as false-positives, said remaining abnormality candidates includes means for eliminating those abnormality candidates having an average edge-gradient value above a first predetermined threshold, a standard deviation of edge-gradient orientation less than a second predetermined threshold value, a circularity less than a third predetermined threshold value and a shape irregularity value greater than a fourth predetermined threshold value.

9. The system according to claim 7, wherein said means for eliminating, as false-positives, said remaining abnormality candidates includes means for eliminating abnormality candidates having a standard deviation of edge-gradient orientation parameter greater than a fifth predetermined threshold value and two narrow peaks at a 180° separation of said edge-gradient orientation distribution.

10. The system according to claim 7, wherein said means for eliminating, as false-positives, said remaining abnormality candidates includes means for eliminating abnormality candidates having a contrast value less than a sixth predetermined threshold value with a size greater than a seventh predetermined threshold value, or a contrast value greater than an eighth predetermined threshold value with a size less than a ninth predetermined threshold value.

11. The system according to claim 7, wherein said means for eliminating, as false-positives, said remaining abnormality candidates includes mans for eliminating those candidates for which no transition point is found.

12. The system according to claim 7, wherein said means for eliminating, as false-positives, said remaining abnormality candidates includes means for eliminating abnormality candidates having a circularity less than a tenth predetermined threshold value or a shape irregularity less than an eleventh predetermined threshold value.

* * * * *